US00PP36993P2

(12) United States Plant Patent
Bakhuijzen et al.

(10) Patent No.: US PP36,993 P2
(45) Date of Patent: Sep. 30, 2025

(54) ***CORTADERIA* PLANT NAMED 'Day20'**

(50) Latin Name: *Cortaderia selloana*
Varietal Denomination: Day20

(71) Applicants: David Bakhuijzen, Boskoop (NL); Marcel de Pater, Boskoop (NL)

(72) Inventors: David Bakhuijzen, Boskoop (NL); Marcel de Pater, Boskoop (NL)

(73) Assignee: V.O.F. DAYLIGHT BOOMKWEKERIJ, Boskoop (NL)

( * ) Notice: Subject to any disclaimer, the term of this patent is extended or adjusted under 35 U.S.C. 154(b) by 0 days.

(21) Appl. No.: 18/913,349

(22) Filed: Oct. 11, 2024

(51) Int. Cl.
*A01H 5/02* (2018.01)
*A01H 6/46* (2018.01)

(52) U.S. Cl.
USPC ..... Plt./384

(58) Field of Classification Search
USPC ..... Plt./384
CPC ... A01H 5/02; A01H 5/12; A01H 5/00; A01H 6/46
See application file for complete search history.

(56) References Cited

PUBLICATIONS

Floral Daily 2021 Silver award for golden *Cortaderia*, retrieved on Feb. 5, 2025 at https://www.floraldaily.com/article/9361456/silver-award-for-golden-cortaderia/, one page. (Year: 2022).*
Groen-Direkt Boskoop 2022, retrieved on Feb. 5, 2025 at https://www.groen-direkt.nl/novelties/cortaderia-selloana-day2-tiny-pampa-gold/?lang=en, pp. 2-4. (Year: 2022).*
KVBC retrieved on Feb. 5, 2025 at https://www.kvbc.nl/kvbc-award-silver-for-golden-variegated-cortaderia/?lang=en, 2 pp. (Year: 2025).*
Rice 2021 The first guaranteed dwarf pampas grass, retrieved on Feb. 5, 2025 at https://www.rhs.org.uk/plants/plants-blogs/plants/january-2021/cortaderia-selloana-day1-tiny-pampa, 2 pp. (Year: 2021).*
UPOV Pluto Plant Variety Database 20250204, retrieved on Feb. 5, 2025 at https://pluto.upov.int/result, one page. (Year: 2025).*
Van Vliet New Plants Catalog 2020, retrieved on Feb. 5, 2025 at https://newplants.nl/uploads/Catalogue-2020.pdf, pp. 1-3, 16. (Year: 2020).*

* cited by examiner

*Primary Examiner* — June Hwu
(74) *Attorney, Agent, or Firm* — Penny J. Aguirre

(57) ABSTRACT

A new cultivar of *Cortaderia* plant named 'Day20' that is characterized by its strong and sturdy plant habit, its conspicuously dense and compact plant shape, its floriferous flowering habit with creamy white inflorescences, and its variegated foliage that is margined and axillary striped with yellow-green to grey-yellow.

1 Drawing Sheet

CROSS-REFERENCE TO RELATED APPLICATIONS

This application is also co-pending with a U.S. Plant patent applications filed for plants derived from the same breeding program that are entitled *Cortaderia* Plant Named 'Day 10' (U.S. Plant Pat. No. 36,606).

Botanical classification: *Cortaderia selloana.*

Cultivar designation: 'Day20'.

BACKGROUND OF THE INVENTION

The present invention relates to a new and distinct cultivar of *Cortaderia selloana* and will be referred to hereafter by its cultivar name, 'Day20'. 'Day20' represents a new perennial ornamental grass grown for landscape use.

'Day 20' was discovered by the Inventors as a naturally occurring branch mutation of *Cortaderia selloana* 'Day 10' that was growing in a production field in Boskoop, The Netherlands in July of 2022.

Asexual propagation of the new cultivar was first accomplished by division by one of the Inventors in July of 2022 in Boskoop, The Netherlands. Asexual propagation by division has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Day20' as a unique cultivar of *Cortaderia.*

1. 'Day20' exhibits a strong and sturdy plant habit.
2. 'Day20' exhibits a conspicuously dense and compact plant shape.
3. 'Day20' exhibits a floriferous flowering habit with creamy white inflorescences.
4. 'Day20' exhibits variegated foliage that is margined and axillary striped with yellow-green to grey-yellow.

The parent plant of 'Day20' differs from 'Day20' in having foliage that is all green (non-variegated) in color and inflorescences that are beige-white in color. 'Day20' can be most closely compared to the *Cortaderia* cultivars 'Monrin' (U.S. Plant Pat. No. 5,136), 'Splendid Star' (U.S. Plant Pat. No. 16,277) and 'Day2' (not patented). 'Monrin' is similar to 'Day20' in having variegated foliage and creamy white inflorescences. 'Monrin' differs from 'Day20' in having a taller plant height, variegated foliage with green margins and more irregular axillary stripes of yellow, less inflorescences, and flowering that is less consistent. 'Splendid Star' is similar to 'Day20' in having a compact plant shape. 'Splendid Star' differs from 'Day20' in having foliage that non-variegated and all yellow in color, less inflorescences, and flowering that is less consistent. 'Day2' is similar to 'Day20' in having a dense plant habit. 'Day2' differs from 'Day20' in having a more compact plant habit and a shorter flowering period as the mature inflorescences fade more quickly and to a more brown color.

BRIEF DESCRIPTION OF THE DRAWING

The accompanying color photograph illustrates the overall appearance and distinct characteristics of the new *Cortaderia*. The photographs were taken of a plant 2-years-in-age as grown outdoors in a 30-cm container in Boskoop, The Netherlands.

The photograph provides a side view of a plant of 'Day20' in bloom.

The colors in the photograph are as close as possible with the photographic and printing technology utilized and the color values cited in the Detailed Botanical Description accurately describe the colors of the new *Cortaderia*.

DETAILED BOTANICAL DESCRIPTION

The following is a detailed description of 1-year-old plants of the new cultivar as grown outdoors in a 21-cm container in Boskoop, The Netherlands. The phenotype of the new cultivar may vary with variations in environmental, climatic, and cultural conditions, as it has not been tested under all possible environmental conditions. The color determination is in accordance with the 2019 (reprint of 2015) Colour Chart of The Royal Horticultural Society, London, England, except where general color terms of ordinary dictionary significance are used.

General description:

*Blooming period.*—8 weeks; late summer into fall in The Netherlands.

*Plant type.*—Herbaceous, ornamental perennial grass.

*Plant habit.*—Clump-forming, compact, upright with cascading foliage.

*Height and spread.*—Average of 54.5 cm in height from the soil level to the top of the foliar plane, average of 56 cm in height from the soil level to the top of the floral plane, 92 cm in diameter as grown in a container and 1 m in height and spread as grown in the landscape.

*Cold hardiness.*—At least in U.S.D.A. Zone 7.

*Diseases and pests.*—No susceptibility or resistance to diseases or pests has been observed.

*Root description.*—Thin, fleshy, no stolons or rhizomes present.

*Root development.*—Average of 8 weeks to produce a young rooted plant in spring from a division.

*Propagation.*—Division.

*Growth rate.*—Moderate to highly vigorous.

Branch description (basal shoots):

*Branching.*—Average of 29 basal shoots.

*Branch size.*—6.5 cm in length (consisting of sheaths; measured from base of shoot to base of uppermost leaf blade), 4 cm in diameter.

*Branch shape.*—Rounded.

*Branch surface.*—Slightly glossy.

*Branch strength.*—Very strong.

*Branch color.*—Young; 145B, mature; 146B to 146C, internodes; N144A.

*Branch aspect.*—Average angle: 35° (varying between 0° (=vertical) and 70°).

*Internode length.*—1 cm.

Foliage description:

*Leaf shape.*—Linear.

*Leaf quantity.*—8 per shoot.

*Leaf division.*—Simple.

*Leaf base.*—Sheathing; 5.6 cm in length, 4 mm in width, color; 146B to 146C, margins 148D.

*Leaf apex.*—Narrow and long acuminate.

*Leaf aspect.*—Moderately carinate.

*Leaf venation.*—Parallel, both surface N138C.

*Leaf margins.*—Entire, but very sharp when rubbed downwards; due to very small and very sharp teeth.

*Leaf size.*—44 cm in length, 7 mm in width.

*Leaf (blade and sheath) surface.*—Both surfaces non-rugose, matte, glabrous and smooth, ligules hairy, average length of hairs is 1 mm, NN155B in color.

*Leaf arrangement.*—Alternate.

*Leaf color.*—Leaves variegated; Young upper surface 144B, margins and axillary striped 1A, young lower surface 145A, margins and axillary striped 154B to 154C, mature upper surface N138B, margins and axillary striped 151D, 154A, 154B, and 160C, mature lower surface NN137C, margins and axillary striped 153D, 160B, and 160C.

Flower description:

*General description.*—Compact, panicle.

*Lastingness of inflorescence.*—Average of 1 month for spikelets to drop, persistent.

*Fragrance.*—None.

*Panicle size.*—Average of 17.8 cm in length and 6.4 cm in diameter.

*Flower number.*—An average of 2,500 flowers per inflorescence, 12,000 flowers per plant.

*Flower buds.*—An average of 2 mm in length, enclosed by 1 palea, 1 awn and many lemma, average length 9 mm, 1 mm in diameter, linear in shape, smooth and glabrous surface, matte, color; 145C with glume and lemma a color between 156D and 157D.

*Peduncle.*—43 cm in length, 3.25 mm in diameter, very strong, held in an angle of 10° to soil level, surface smooth, matte, glabrous, and N144A in color.

*Pedicels.*—1.5 mm in length, 0.5 mm in diameter, moderately strong, held in an angle of 10° to soil level, surface smooth, matte, glabrous, and 148D in color.

*Spikelet description (flowers).*—Spikelet consisting of a single palea; shaped linear, 3 mm in length, 1 mm in width, top narrow acute, base cuneate, margins entire, both surfaces N144A in color, glume an average of 1 cm in length, single awn elongated to an average of 9 mm in length, glabrous, slightly glossy, 156C in color, an average of 30 lemma placed at the base of each palea, hair-like, average of 6 mm in length, 156D in color.

Reproductive organs:

*Androecium.*—Stamens; average of 2, anthers; basifixed and feather-like in shape, 1 mm in length, 0.4 mm in width, N199B in color, filament; 1 mm in length, 199A in color, pollen; none observed.

*Gynoecium.*—Pistil; none observed.

*Seed.*—None observed.

It is claimed:

1. A new and distinct cultivar of *Cortaderia* plant named 'Day20' as herein illustrated and described.

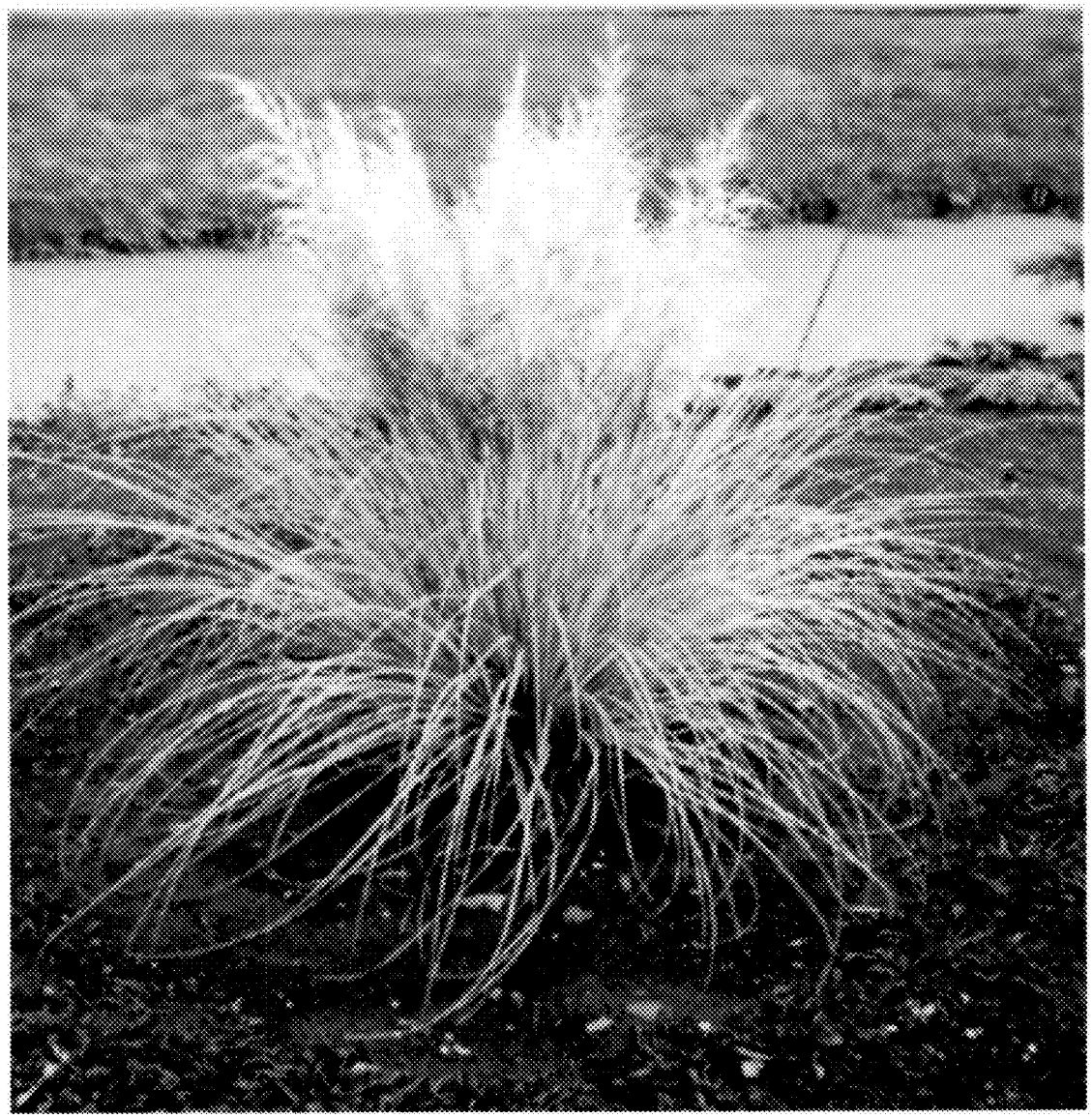

* * * * *